(12) United States Patent
Schildkraut et al.

(10) Patent No.: US 11,786,193 B2
(45) Date of Patent: Oct. 17, 2023

(54) METAL ARTIFACTS REDUCTION IN CONE BEAM RECONSTRUCTION

(71) Applicant: CARESTREAM DENTAL LLC, Atlanta, GA (US)

(72) Inventors: Jay S. Schildkraut, Rochester, NY (US); Jean-Marc Inglese, Bussy-Saint-Georges (FR)

(*) Notice: Subject to any disclaimer, the term of this patent is extended or adjusted under 35 U.S.C. 154(b) by 290 days.

(21) Appl. No.: 17/419,081

(22) PCT Filed: Dec. 29, 2019

(86) PCT No.: PCT/US2019/068861
§ 371 (c)(1),
(2) Date: Jun. 28, 2021

(87) PCT Pub. No.: WO2020/142397
PCT Pub. Date: Jul. 9, 2020

(65) Prior Publication Data
US 2022/0110596 A1    Apr. 14, 2022

Related U.S. Application Data

(60) Provisional application No. 62/786,463, filed on Dec. 30, 2018.

(51) Int. Cl.
*A61B 6/00* (2006.01)
*A61B 6/03* (2006.01)
*A61B 6/14* (2006.01)

(52) U.S. Cl.
CPC ............ *A61B 6/4085* (2013.01); *A61B 6/032* (2013.01); *A61B 6/145* (2013.01); *A61B 6/5205* (2013.01); *A61B 6/5258* (2013.01)

(58) Field of Classification Search
CPC ....... A61B 6/4085; A61B 6/032; A61B 6/145; A61B 6/5205; A61B 6/5258; A61B 5/0073; A61B 6/14; A61B 6/5247; G06T 11/005
See application file for complete search history.

(56) References Cited

U.S. PATENT DOCUMENTS

| 8,023,767 | B1 * | 9/2011 | Ning | G06T 7/12 382/128 |
| 8,971,605 | B2 * | 3/2015 | Hsieh | G06T 7/0012 378/4 |
| 2014/0227655 | A1 * | 8/2014 | Andreiko | A61B 5/0088 433/29 |

FOREIGN PATENT DOCUMENTS

WO    WO-2013129811 A1 *    9/2013    ............ A61B 6/032

* cited by examiner

*Primary Examiner* — Courtney D Thomas

(57) ABSTRACT

The present disclosure describes methods and apparatuses for reducing metal artifacts in cone beam computed tomography (CBCT) reconstructions. The methods use multiple imaging modalities to identify and locate metal present in a region of dental patients mouth and to generate a reconstructed 3-D volume image of the region with reduced metal artifacts using data obtained by the multiple modalities. According to example embodiments, the methods include creating a metal map using data from a first imaging modality and an initial 3-D reconstruction from data obtained from a second imaging modality including CBCT imaging. The metal map is registered to the initial 3-D reconstruction with a reconstructed metal map and projection metal maps being subsequently produced and applied to projections from the CBCT imaging to generate interpolated projections. An artifact reduced 3-D reconstruction is produced from the interpolated projections and a final 3-D reconstruction is created therefrom including merged metal information.

14 Claims, 3 Drawing Sheets

METAL ARTIFACTS REDUCTION IN CONE BEAM RECONSTRUCTION

FIELD OF THE INVENTION

The present invention relates generally to the fields of dental imaging and of image reconstruction methods and apparatuses for Cone-Beam Computed Tomography (CBCT) imaging. More specifically, the present invention relates to methods and apparatuses for improving CBCT images by reducing metal artifacts in reconstructed images.

BACKGROUND OF THE INVENTION

Three-dimensional (3-D) volume imaging can be a valuable diagnostic tool that offers significant advantages over earlier two dimensional (2-D) radiographic imaging techniques for evaluating the condition of teeth and bone. Three-dimensional (3-D) imaging of a patient or other subject has been made possible by a number of advancements, including the development of high-speed imaging detectors, such as digital radiography (DR) detectors that enable multiple images to be taken in rapid succession.

Cone beam computed tomography (CBCT) (also sometimes referred to herein as cone beam CT) technology offers considerable promise as one type of diagnostic tool for providing three-dimensional (3-D) volume images. Cone beam X-ray systems are used to produce three-dimensional (3-D) images of the teeth of dental patients for the purposes of diagnosis, treatment planning, reconstruction, and various other purposes. Cone beam CT systems capture volume data sets by using a high frame rate flat panel digital radiography (DR) detector and an x-ray source, typically affixed to a gantry that revolves about the subject to be imaged. The cone beam CT system directs, from various points along its orbit around the subject, a divergent cone beam of x-rays through the subject and to the detector. The cone beam CT system captures projection images throughout the source-detector orbit, for example, with one two-dimensional (2-D) projection image at every degree increment of rotation. The projections are then reconstructed into a three-dimensional (3-D) volume image using various methods. Among the most common methods for reconstructing the three-dimensional (3-D) volume image from two-dimensional (2-D) projections are filtered back projection (FBP) and Feldkamp-Davis-Kress (FDK) methods.

Although three-dimensional (3-D) images of diagnostic quality can be generated using CBCT systems and technology, a number of technical challenges remain. Highly dense objects, such as metallic implants, appliances, surgical clips and staples, dental fillings, and the like can cause various image artifacts that can obscure useful information about the imaged tissue. Dense objects, having a high atomic number, attenuate X-rays in the diagnostic energy range much more strongly than do soft tissue or bone features, so that far fewer photons reach the imaging detector through these objects. For three-dimensional (3-D) imaging, the image artifacts that can be generated by metallic and other highly dense objects include dark and bright streaks that spread across the entire reconstructed image. Such artifacts can be due to physical effects such as high noise, photon starvation, radiation scatter, beam hardening, the exponential edge-gradient effect, aliasing, and clipping, and non-linear amplification in FBP or other reconstruction methods. The image degradation commonly takes the form of light and dark streaks in soft tissue and dark bands around and between highly attenuating objects. These image degradations are commonly referred to as artifacts because they are a result of the image reconstruction process and only exist in the image, not in the scanned object. These artifacts not only conceal the true content of the object, but can be mistaken for structures in the object. Artifacts of this type can reduce image quality by masking other structures, not only in the immediate vicinity of the dense object, but also throughout the entire image. At worst, this can falsify CT values and even make it difficult or impossible to use the reconstructed image effectively in assessing patient dental condition or for planning suitable treatment.

Dental volume imaging can be particularly challenging because of the relative complexity of structures and shapes and because objects of very different densities are closely packed together in a relatively small space. Various types of fillings, implants, crowns, and prosthetic devices of different materials can be encountered during the scan. Beam hardening effects can also impact image quality. Thus, metal artifacts reduction can be particularly difficult for dental volume imaging.

The reduction of artifacts that are caused by metal and other highly attenuating objects is an essential part of a dental cone beam CT scanner, particularly with the increasing use of implants in dental treatments. Methods of reconstructing projections that are acquired with a cone beam scan which have reduced metal artifacts have been developed. These metal artifact reduction (MAR) methods are very effective and can significantly improve the quality of the reconstructed volume. However, the effectiveness of MAR cone beam reconstruction methods depends on the critical step of determining the location of metal in an initial reconstruction of a scanned object. This step is very difficult and error prone because the initial reconstruction often has severe metal artifacts which can be mistaken for metal. When this occurs, these artifacts will be retained in the final MAR reconstructed volume.

Therefore, there is a need in the industry for methods and apparatuses for metal artifact reduction in cone beam scans that solves these and other related problems, difficulties and shortcomings of the current technology.

SUMMARY OF THE INVENTION

Broadly described, the present invention comprises methods and apparatuses for metal artifact reduction in cone beam computed tomography (CBCT) reconstructions. According to example embodiments of the present invention described herein and without limiting the scope of the present invention, the methods and apparatuses are directed at improving the localization and identification of metal in a dental patient so that metal artifact reduction for a cone beam CT scan can be improved. The methods use data from a prior first image using a first imaging modality (such as, but not limited to, an intraoral optical scan, an optical computed tomography (OCT) scan, an ultrasound scan, or other depth-resolved imaging scan) of a patient's mouth (or a desired region of the patient's mouth) in combination with a cone beam CT scan (e.g., a second image produced using a second imaging modality) of the patient's mouth (or a desired region of the patient's mouth) to localize or identify any metal in the patient's mouth or region of interest, to accurately determine the location of metal in an initial reconstructed three-dimensional (3D) volume, and to improve metal artifact reduction in a finally reconstructed three-dimensional (3D) volume.

Other features and advantages of the present invention will become apparent from reading the following description of the non-limiting, example embodiments with reference to the appended drawings.

DETAILED DESCRIPTION OF THE EXAMPLE EMBODIMENTS

Figure 1:
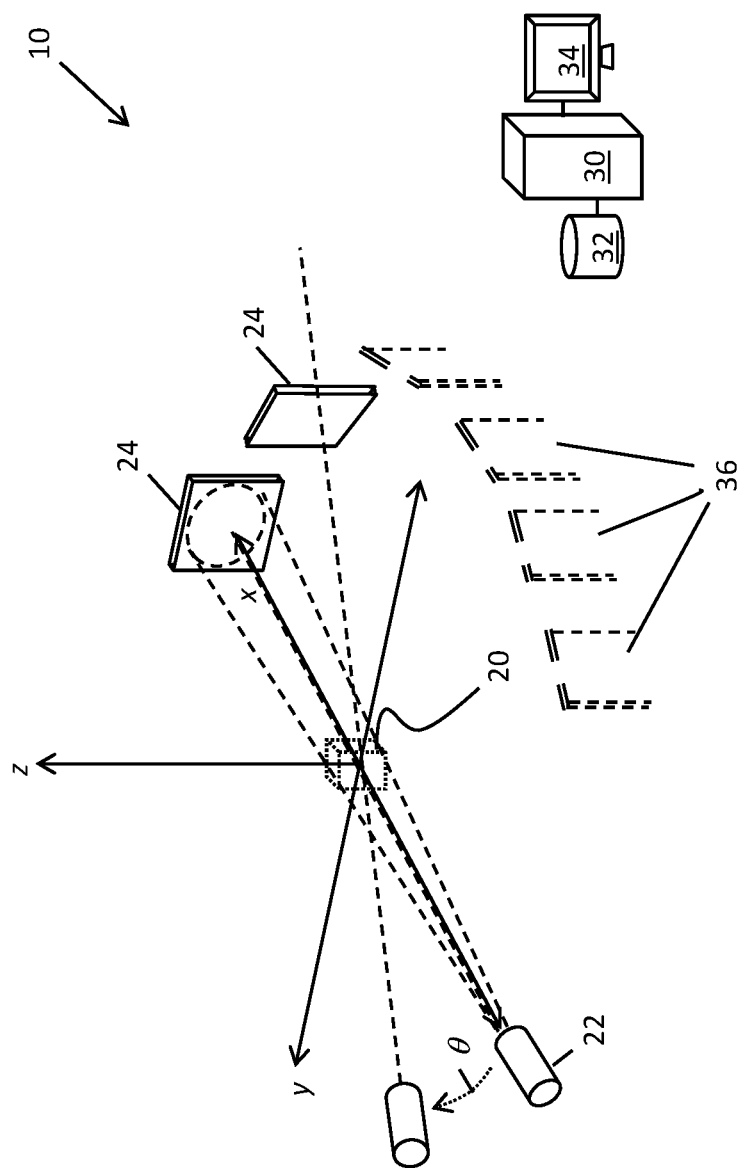
FIG. 1 displays a perspective, schematic view of a cone beam computed tomography (CBCT) system in operation, according to an example embodiment of the present invention, obtaining individual two-dimensional (2-D) projection images that are used to form a three-dimensional (3-D) volume image.

Example embodiments of the present invention are described below in detail with reference being made to the drawings in which like numerals identify like elements or steps throughout the several views. In the following detailed description, the terms "first", "second", and so on, do not necessarily denote any ordinal or priority relation, but are simply used to more clearly distinguish one element from another. Also, the term "volume image" is synonymous with the terms "3-dimensional image" or "3-D image". The example embodiments of the present invention are particularly well suited for suppressing the types of metal artifacts that occur in 3-D volume images, including cone beam computed tomography (CBCT) images as well as fan beam computed tomography (CT) images.

For the image processing steps described herein, the terms "pixels" for picture image data elements conventionally used with respect two-dimensional (2-D) imaging, such as the pixels of an X-ray detector or image display, and "voxels" for volume image data elements often used with respect to 3-D imaging, can be used interchangeably. It should be noted that the 3-D volume image is itself synthesized from image data obtained as pixels on a 2-D sensor array and displays as a 2-D image from some angle of view. Thus, 2-D image processing and image analysis techniques can be applied to the 3-D volume image data. In the description that follows, methods described as operating upon pixels may alternately be described as operating upon the 3-D voxel data that is stored and represented in the form of 2-D pixel data for display. In the same way, methods that operate upon voxel data can also be described as operating upon pixels.

In the context of the present disclosure, the noun "projection" may be used to mean "projection image", referring to the 2-D X-ray image that is captured and used to reconstruct the volume image. In addition, "projection" can also refer to calculated projections for a simulated cone beam system that are obtained by calculating the attenuation of X-rays as they propagate through a 3-D image volume.

As described briefly above, the present invention comprises methods for reducing artifacts in X-ray cone beam computed tomography reconstructions that are caused by metal and other highly X-ray attenuating materials such as those used for implants that are placed within the body. In the context of the present disclosure, high-density objects that cause what is commonly known as metal artifacts in the volume image are termed "metal" objects. This includes objects formed from materials having a relatively high attenuation coefficient. The attenuation coefficient for a material is not a fixed value, but varies and is dependent, in part, on the photon energy level. A titanium metal object has, for example, an attenuation coefficient of about 0.8 cm$^{-1}$ in the 80 KeV range. Bone has, for example, a typical attenuation coefficient of about 0.6 cm$^{-1}$ in the 80 KeV range. Any object having attenuation at or near that of titanium or higher can be considered to be a metal object. It should be noted, for example, that objects formed from some types of highly dense composite materials can have a similar effect on image quality as objects formed from metal or alloys. The methods of the present invention address the type of artifact generated by such objects, of whatever material type or other composition. Materials commonly used and known to cause at least some type of "metal artifact" in radiographs and volume images include metals such as iron, cobalt, chromium, titanium, tantalum, and alloys including cobalt chromium alloys, for example, as well as some ceramic compositions and various composite materials such as high-density composite plastics. Examples of typical implants include, but are not limited to, various types of prostheses, pins, plates, screws, nails, rods, caps, crowns, bridges. fixtures, braces, dentures, and fillings. The implants are usually comprised of metal and/or ceramic material.

CBCT imaging systems and imaging methods used to obtain 3-D volume images using such systems are well known in the diagnostic imaging art and are, therefore, not described in detail herein. Some example methods and techniques for forming 3-D volume images from the source 2-D images, projection images that are obtained in operation of the CBCT imaging systems can be found in various patents and technical papers.

In typical CBCT imaging systems, a computer or other type of dedicated logic processor for obtaining, processing, and storing image data is part of the system, along with one or more displays for viewing image results. A computer-accessible memory is also provided, which may be a memory storage device used for longer term storage, such as a device using magnetic, optical, or other data storage media. In addition, the computer-accessible memory can comprise an electronic memory such as a random access memory (RAM) that is used for shorter term storage, such as employed to store a computer program having instructions for controlling one or more computers to practice the methods of the present invention.

In order to more fully understand the methods of the present invention and the problems addressed, it is instructive to review principles and terminology used for CBCT image capture and reconstruction. Referring to FIG. 1 in which enlarged distances are used for clarity, a CBCT imaging system 10 is shown schematically in operation obtaining individual 2-D projection images 36 that are used to form a 3-D volume image. A cone-beam radiation source 22 directs a cone of radiation toward a subject 20, such as a patient or other subject. A sequence of images is obtained in rapid succession at varying projection angles, θ, about the subject, such as one image at each 1-degree angle increment in a 200-degree orbit. A digital radiography (DR) detector 24 is moved to different imaging positions about subject 20 in concert with corresponding movement of radiation source 22. FIG. 1 shows a representative sampling of DR detector 24 positions to illustrate how these images are obtained relative to the position of subject 20. Once the needed 2-D projection images are captured in this sequence, a suitable imaging algorithm, such as filtered back projection (FBP) or other conventional method, is used for generating the 3-D volume image. Image acquisition and program execution are performed by a computer 30 or by a networked group of computers 30 that are in data communication with DR detectors 24. Image processing and storage is performed using a computer-accessible memory 32. The 3-D volume image can be presented on a display 34.

Figure 2:
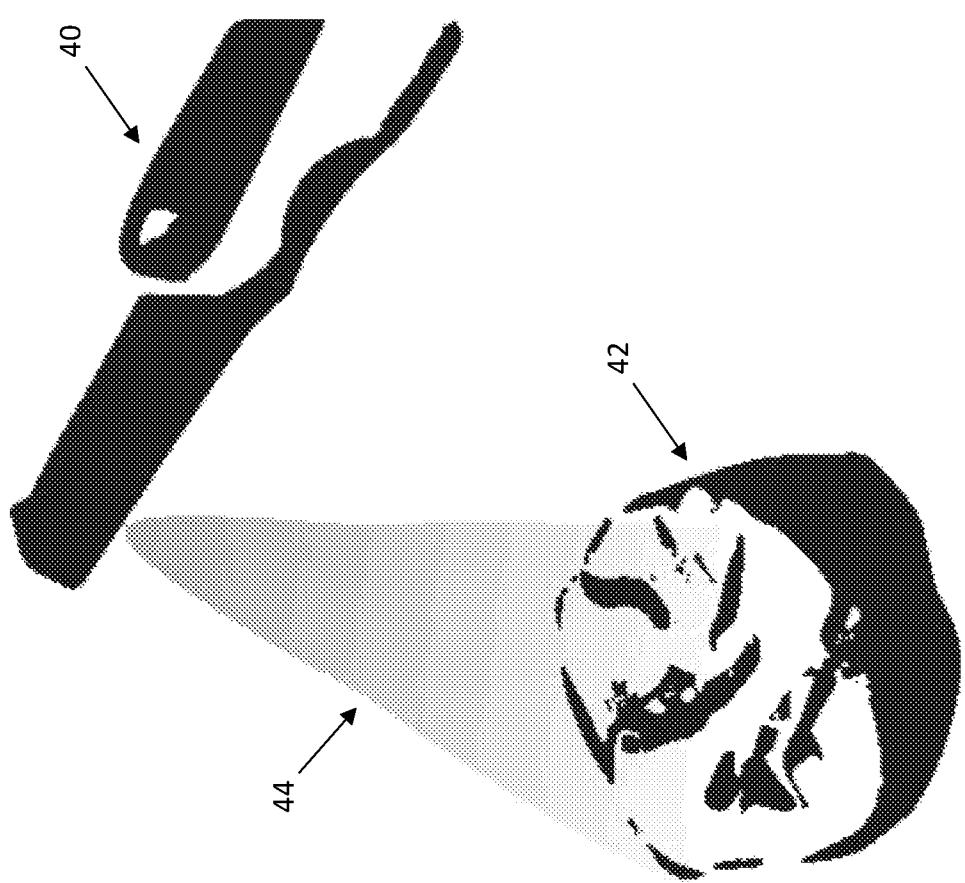
FIG. 2 displays a pictorial view of an intraoral optical scanner in operation, according to an example embodiment of the present invention, scanning a tooth of a dental arch.

FIG. 2 displays a pictorial view of an intraoral optical scanner 40 in operation scanning a tooth 42 of a dental arch. As seen in FIG. 2, structured light 44 is projected onto the tooth 42 and other teeth in the scanned region of the dental arch. An intraoral optical image comprising a surface map of the teeth and surrounding tissue is obtained by triangulation, active wavefront sampling, or strereophotogrammetry of corresponding points in reflected images. The intraoral optical image provides the location of metal within the scanned region without the problems associated with metal artifacts which occur in a cone beam X-ray scan. Although intraoral optical imaging is used in accordance with an example embodiment of the present invention described herein, it should be understood and appreciated that other technologies (including, but not limited to, optical computed tomography (OCT) imaging, ultrasound imaging, or other depth-resolved imaging technologies) may be used in other example embodiments of the present invention to obtain the locations of metal within the scanned region also without the problems associated with metal artifacts.

Figure 3:
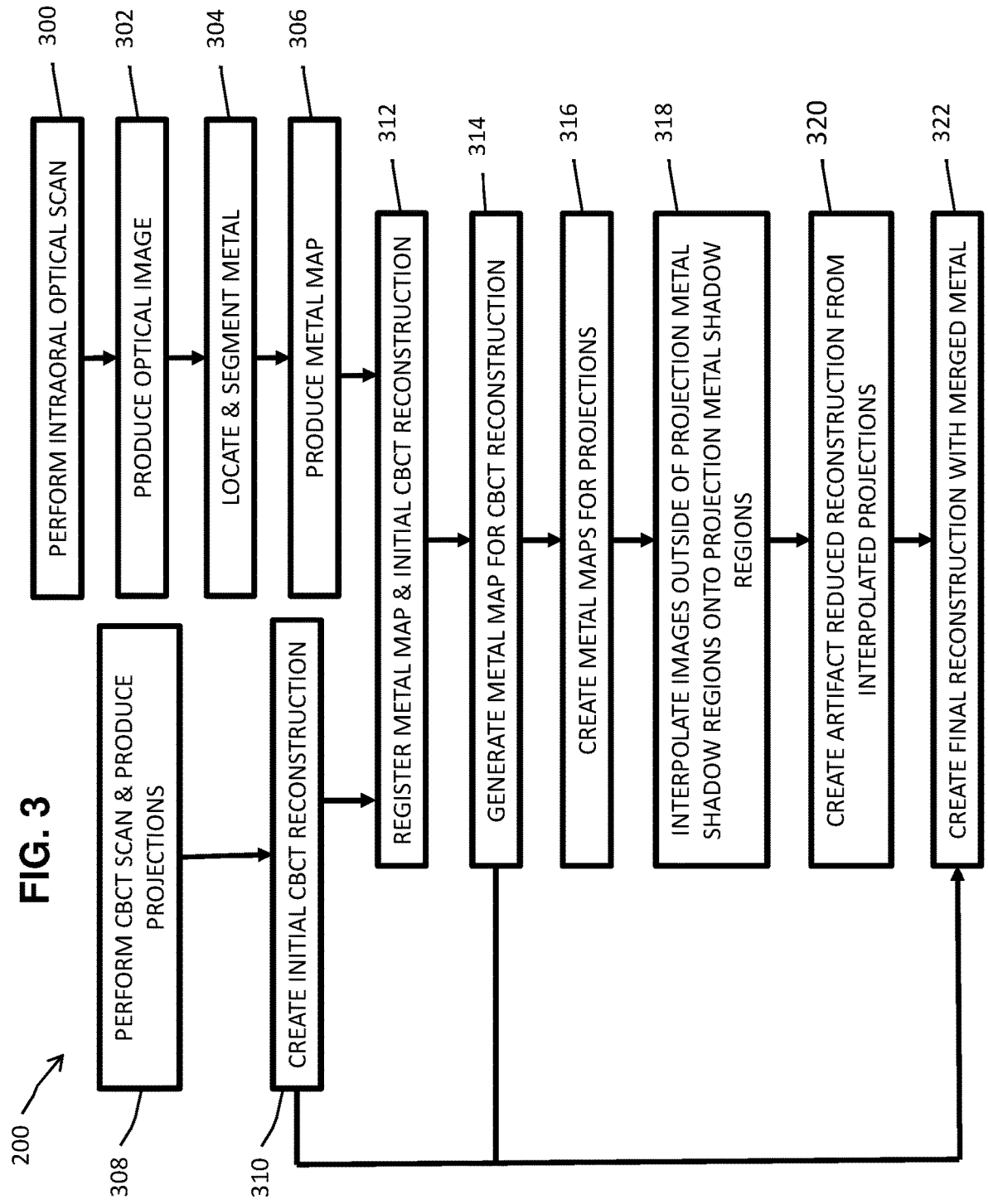
FIG. 3 displays a flowchart representation of a method for reducing metal artifacts in cone beam reconstruction according to an example embodiment of the present invention.

FIG. 3 displays a flowchart representation of a method 200 for reducing metal artifacts in cone beam reconstruction in accordance with an example embodiment of the present invention. Starting at step 300, an intraoral optical scan of the patient is performed to produce optical scan data corresponding to the tooth or teeth in the region of interest of the patient's dental arch. The obtained data is reconstructed, at step 302, to produce an optical image. At step 304, the location of metal in the optical image is determined and, at step 306, a metal map is produced. Subsequently, at step 308, an X-ray cone beam scan of the patient is performed and 2-D cone beam projections are produced. The cone beam projections are reconstructed, at step 310, to create an initial 3-D reconstruction. If the patient has metal or other dense material in their mouth, the initial reconstruction will have artifacts which corrupt the image making it difficult, if not impossible, to determine the location of metal.

Instead of proceeding with a conventional metal artifact reduction method, at step 312, the metal map produced at step 306 from the prior optical image is registered with the initial cone beam 3-D reconstruction. Then, at step 314, a metal map for the cone beam 3-D reconstruction is created using both the initial cone beam 3-D reconstruction from step 310 and the registered metal map from step 312. Continuing at step 316, the metal map for the cone beam 3-D reconstruction is used to create metal maps for the projections acquired at step 308. These metal maps indicate which projection pixels are in the shadow of metal. Next, at step 318, the image outside of the metal shadow regions of the projections are interpolated onto the metal shadow regions to effectively remove metal from the projections. This step includes adding detail to the interpolated projections which may exist within the shadow of metal in the acquired projections. At step 320, the interpolated projections are reconstructed to create a volume image with reduced metal artifacts. This volume image will also not include the metal which is included in the metal map created at step 314. For this reason, at step 322, metal is added from the initial reconstruction created at step 310 to the artifact reduced reconstruction produced at step 320 to create the final reconstruction.

The method 200 for reducing metal artifacts in cone beam reconstruction of the present invention has important advantages over using a single imaging modality alone. The intraoral optical image does not suffer from metal artifacts, but also does not provide the location of metal beneath the surface. On the other hand, the initial reconstruction does have metal artifacts, but also provides an image of the metal within tissue. Combining the information that is contained in the initial reconstruction and registered optical image results in an improved metal mask over what could be produced with either imaging modality alone.

At this juncture, it is important to reiterate that although intraoral optical imaging is used as a first imaging modality in the example embodiment of method 200 described above together with a second imaging modality comprising CBCT imaging, other imaging modalities or technologies (including, but not limited to, optical computed tomography (OCT) imaging, ultrasound imaging, or other depth-resolved imaging technologies) may be used as a first imaging modality in other example embodiments of the present invention in lieu of intraoral optical imaging to obtain the locations of metal within the scanned region and produce an initial metal map similar to the metal map produced at step 306. It should be understood and appreciated that while the present invention has been described herein with respect to the above example embodiments, the present invention may be embodied in other example embodiments that include variations from the above-described methods and apparatuses that are still within the scope of the present invention.

What is claimed is:

1. A method for reducing metal artifacts in a volume radiographic image of a region which includes at least a part of a dental arch and surrounding tissue, the method comprising the steps of:
   acquiring an intraoral optical image of the region;
   acquiring an X-ray cone beam scan of the region;
   registering the intraoral optical image with a reconstructed volume of the X-ray cone beam scan;
   identifying the location of metal in the reconstructed volume using the registered optical intraoral image; and
   using the identified location of metal in the reconstructed volume to reduce metal artifacts in a subsequent reconstructed volume of the cone beam scan.

2. The method of claim 1, wherein the step of acquiring an intraoral optical image is performed prior to the step of acquiring an X-ray cone beam scan of the region.

3. The method of claim 1, wherein prior to the step of registering, the method further comprises a step of producing a metal map including the locations of metal identified in the intraoral optical image.

4. The method of claim 1, wherein prior to the step of registering, the method further comprises a step of generating a reconstructed volume from the cone beam scan.

5. The method of claim 1, wherein the method further comprises a step of creating metal maps for projections obtained from the cone beam scan.

6. The method of claim 5, wherein the metal maps indicate which projection pixels are in the shadow of metal.

7. The method of claim 5, wherein the method further comprises a step of interpolating image portions outside of metal shadow regions of the projections onto metal shadow regions of the projections to create interpolated projections.

8. The method of claim 7, wherein the method further comprises a step of reconstructing a volume image with reduced metal artifacts from the interpolated projections.

9. The method of claim 8, wherein the method further comprises a step of creating a final reconstructed volume image by adding metal from a reconstructed volume generated from the cone beam scan to the reconstructed volume image produced from the interpolated projections.

10. A method for reducing metal artifacts in a volume radiographic image of a region which includes at least a part of a dental arch and surrounding tissue, the method comprising the steps of:

acquiring an image of the region using a first imaging modality;

acquiring an X-ray cone beam scan of the region;

registering the image with a reconstructed volume of the X-ray cone beam scan;

identifying the location of metal in the reconstructed volume using the registered image; and using the identified location of metal in the reconstructed volume to reduce metal artifacts in a subsequent reconstructed volume of the cone beam scan.

11. The method of claim 10, wherein the first imaging modality comprises intraoral optical imaging.

12. The method of claim 10, wherein the first imaging modality comprises optical computed tomography (OCT) imaging.

13. The method of claim 10, wherein the first imaging modality comprises ultrasound imaging.

14. The method of claim 10, wherein the first imaging modality comprises depth-resolved imaging.

\* \* \* \* \*